United States Patent [19]
Corliss et al.

[11] Patent Number: 4,822,595
[45] Date of Patent: Apr. 18, 1989

[54] HOOF LOTION

[76] Inventors: Lyal S. Corliss; James W. Nielsen, both of P.O. Box 6669, Brookings, Oreg. 97415

[21] Appl. No.: 897,995

[22] Filed: Aug. 19, 1986

[51] Int. Cl.⁴ .................. A61K 7/04; A61K 33/40; A61K 33/34; A61K 33/18

[52] U.S. Cl. .................................. 424/61; 424/130; 424/141; 424/150

[58] Field of Search ................ 424/61, 130, 150, 141

[56] References Cited

U.S. PATENT DOCUMENTS 2,887,116  5/1959  Wooding .............................. 424/61
3,989,817  11/1976  Mayer .................................. 424/61

Primary Examiner—Frederick E. Waddell

[57] ABSTRACT

A composition and method is disclosed for healing, preserving and penetration, and killing and preventing fungus growth on mammals with ungulates. In the preferred embodiment hoof lotion with a composition of linseed oil, lanolin, terpentine, pine tar, hydrogen peroxide, iodine and copper sulphate are blended and dissolved in a biocidal solution. It is sprayed on the affected area of the hoof, with a easy to use finger trigger spray nozzle that is fasten to a hand held bottle, to which the lotion in amounts sufficient to prevent fungi and the protection and maintenance of health on said mammals with ungulates adheres. Is evenly distributed in the composition such that the dispersal is uniformly. It is highly effective for killing and preventing fungal growths, and it heals cracks, brittle surfaces, dryness, and moisture problems in and around the coronet bands, sole, frog, walls, and heel. It is fast acting, quick drying and long lasting, and it is easy to apply, inexpensive to use and lacks the draw backs of prior methods, and composition.

1 Claim, No Drawings

HOOF LOTION

The invention relates generally to the preservation and maintenance of Mammals having ungulates and the undesired growths of fungi, cracks, dryness, brittleness and the like on hoofs and other outside surfaces exposed to the atmosphere and terrain and particularly to an improved method and use composition for a lotion treatment on such surfaces.

In very moist climates, the growth of fungi and the absorption of moisture in and on the hoofs occurs. In very dry climates cracks, brittleness and dry hoof conditions occurs. Such condition cause damage to the hoofs and do not permit for a healthy hoof and do not permit the surface to grow properly and can cause a variety of problems depending on the nature of the surface. In particular, fungi, cracks, dryness and too much moisture will not allow for a healthy hoof and eventually causes accerlerated decomposition of the hoof, this permits moisture absorbtion in wet climate and dryness in dry climate which can damage the hoofs support structure and internal hoof problems. The resultant damage is very expensive, painful to the mammals, time consuming and sometimes crippling to repair. Similarly, fungi growth in and along the coronet bands, walls, frog, sole, heel and cracks and dry hoof is painful, unhealthy and unsightly and can foster additional undesired growths and can accelerate decomposition of the hoof. The animal can also become lame, increasing the risk of injury to the hoof and legs. Hoof problems can be painful to the animals, unhealthy, unsightly and foster undesired problems of an unhealthy nature. Consequently, it is desirable to maintain a healthy hoof to prevent, fungi growth, cracking, dryness and too much moisture on these surfaces for a healthy hoof.

Various attempts have been made to maintain a healthy hoof. Certain other ointments such as; tallow, soya oil, petroleum, aloe vera, bees wax, neatsfoot, glycerine, coconut oil, castor oil, olive oil, natural rosemary oil, purefied softened water and stearamido propyl dimethylamine lactate have been used with varying degrees of success, but also, with numerous drawbacks. Ointments and creams such as; Absorbine Hooflex, Alo-Hoof and Hoofmaker are such products; but the applications are usually uneven and don't penetrate, do not prevent fungi, they also cause dirt and such to cling to it and they don't dry well, are hard to apply the products into the coronet bands, the walls, the frog, sole, heels and cracks, thus require frequent reapplication. Such creams and ointments can get all over your hands and skin causing a mess, they necessitating precautions during application. Absorbine Hooflex is like tar and very hard to apply and will not prevent fungi. Hoofmaker is like cold cream and difficult to get into the coronet band, walls, frog, heel and will not kill fungi. Aloe-Hoof has a shoe polish applicator, this is very difficult to apply to the coronet bands, frog, sole and heel and will not penetrate into the walls and will not kill fungi. Such compounds are also unsuitable because they tend to get messy, wasteful and difficult to apply to the hoofs.

Ungulates or hoofed animals Mammals have been treated with coal tar to aloe vera creams and ointments and many have been proven unsatisfactory for treating established hoof problems.

Absorbine Hooflex contains the contents of the following; Active Ingredients are; petroleum, neatsfoot oil, lanolin, tallow, turpentine, soy oil, pine tar, wax, rosin, phenol 0.32 as a preservative. Net. wt. 14 oz. by W. F. Young Inc. Absorbine Hooflex is very difficult to apply to the hoof, it is a tar base and a spoon is needed to dig the material out of the metal can. It is difficult to get this product into the cracks or brittle areas on the walls sole, coronet bands, frog, heel or the hoof and it gets all over your hands and skin and also, this product will not prevent fungus growths.

Aloe-Hoof is a product with the contents of; aloe vera and mink oil. This product is for hoof treatments. It comes with a shoe applicator that drys out after one application. It is difficult to apply this product into the crevises, coronet bands, frog, sole, heel and walls and cracks of the hoof. This product is produced by Farnham Companies Inc. Omaha, Nebraska 68112. Aloe-Hoof comes in a 8 Oz. bottle.

Another product is Hoofmaker by Straight Arrow Inc. address at Phillipsburg, N.J. 08865; The formula is purified softened water emulsifying wax, quaternium 18, stearamido propyl dimethylamine lactate, steryl wax, cetyl wax, glycerine, coconut oil, soybean oil, castor oil, olive oil, lanolin, cottonseed oil, protein, methyl paraben, propyl paraben and C yellow #5 and Yellow #6 and natural rosemary oil. Hoofmaker comes in a 32 oz. container. The product feels like cold cream in a deep jar, it is difficult to get the material out of the jar and it gets on your hands and skin. It is also very difficult to get into the cracks and deep areas around the coronet bands, frog, sole, walls, heel and cracks and deep areas in and around the hoof, it is also very difficult to spread the material evenly, it is very slow drying, slow acting, and because it is slow drying the product attracts dirt and dust and finally; the product is not effective on fungus.

Accordingly, a need remains for an effective method for preventing fungal growth, a method for healing, a method that will penetrate, and a method for healing cracks, brittle surface, drying and dryness, moisture problems in and around the coronet bands, sole, frog, wall and heel of the hoof, a material that is fast acting, quick drying and long lasting, is easy to apply and relatively inexpensive and additionally lacks the drawbacks of prior methods.

SUMMARY OF THE INVENTION

It is a principal object of the invention to improve upon prior methods and composition of preserving the health of a mammal with ungulates.

Another object of the invention is to provide a universal method which will inhibit fungi growths.

Yet another object of the invention is to provide a method for healing the hoof.

A further object is to provide a lotion for hoofs which is inexpensive and easy to apply.

Another object of the invention is to provide a method for a method for easy application without touching the hands or skin and without any of the drawbacks of prior methods and compositions.

It is also an object of the invention to provide a product that is fast drying.

It is a further object to provide a method of application and a product which is safe for humans and animals and therefore can be applied without taking special precautions.

According to the invention, a animal hoof; mammal with ungulates lotion used for maintaining a healthy hoof is disclosed which can be applied with an easy to use trigger spray. The nozzle with a trigger spray is attached to a bottle and by pulling your finger on the trigger can easily spray the contents of the bottle into and onto the surface of the hoof, such as by spray bottle. To make the lotion, the active ingredients are selected from a group of substance which dissolve in themselves in minute concentration to form a biocidal solution effective for easy spraying. Such lotion is finely mixed in predetermined proportions and heated and blended into a composition. Besides uniformly dispersing while heating the resulting mixture prevents caking or settling of the lotion while stored in the bottle for easy ready to use. The lotion preferably has the characteristic of adhering to a surface and drying quickly after being conveyed to the surface to be treated. The lotion material also; preferably holds the adhering particles in close proximity to each other on the treated surface to encourage healing and preserving upon contact, while penetrating deep. The material provides such long lasting health to animals. The material which provides such characteristics and additionally acts as a carrier and drys the lotion quickly and yet which kills fungi growth.

The lotion mixture according to the present invention is sprayed on uniformally in a wet liquid composition onto the hoof to be treated. The fine biocidal solution lotion permeates the cracks and crevices while penetrating that of the hoofs coronary band, walls, frog, heel, sole and under and on the top surface of the hoof, thus preventing fungi, healing and preserving the hoof. Over time the lotion protects and as the hoof grows the lotion will easily disperse.

Dissolution of the lotion is preferably enhanced by using seven different ingredients such as; linseed oil, turpentine, lanolin, iodine, pine tar, hydrogen peroxide and copper sulphate. With such a combination, biocidal ions are dissolved more quickly in the lotion on contact to the hoof. The copper salts are preferably mixed in proportion to their relative efficacy against fungi. Prompt generation of a biodicdal solution is greatly enhanced by the area it comes into contact with, the dissolution of copper salt enabling fungi growth to be inhibited until the hoof grows and expands. This feature is enhanced by spraying twice a week or so to maintain the lotion on surface contact.

The foregoing and other objects, features and advantages of the invention will become more readily apparent from the following detailed description of the preferred imbodiment.

DETAILED DESCRIPTION

The preferred embodiment utilizes, linseed oil, turpentine, lanolin, iodine, hydrogen peroxide, pine tar and copper sulphate. Such materials are selected primarily because they are all effective in the concentration and solution composition to prevent and protect the surfaces exposed to the atmosphere, terrain, track, barn yard, transporting, stabling and will react to enhance the dissolution of the lotion. In addition, I have discovered that the lotion will kill and prevent fungus growth and also it will act as a antiseptic, it drys quickly, helps moisten, will not harm human skin and also are relatively inexpensive materials.

The material of boiled or raw linseed oil; a yellowish oil from the flax seed and used in paints and printers ink. The linseed oil is used as a protective, elastic coating when dried in this invention.

The use of turpentine; is a resinous and viscid juice of pine and certain other trees and the oil extracted from this is used in paints and varnishes. In this invention it is used as an ointment, a dryer and a protective and local irritant ointment and a solvent resin and rosin polish.

The use of lanolin; the fat of wool from sheep, is a yellow wax-like mass used in making ointments and in this invention is used as a water absorbable base.

The use of iodine, a nonmetallic grayish-black crystalline element of the halogen group, which when heated gives forth fumes of a violet color and in this invention it is used as an antiseptic.

The use of hydrogen peroxide; a colorless syrupy compound of hydrogen and oxygen, often used diluted to bleach or disinfect and in this invention it is used to disinfect.

The use of pine tar; a thick brown liquid distilled from pine wood and used in medication, paints and disinfectants in this invention it will be used as a disinfectant.

The use of copper sulphate; a blue crystalline material used as a antifungal treatment. In this invention copper sulphate will be used to prevent fungal growth and kill fungi.

The Corliss Hoof Lotion is applied in liquid form to the surface of the hoof around and on the; coronary bands, walls, frog, sole, heel, in cracks and crevises of the hoof to help prevent growth of fungi, chafing, cracking, dryness, moisture, chapping and brittleness. If you maintain a flexible hoof, then the hoof has better circulation and more circulation is a healthier hoofed animal.

The ingredients are; The first ingredient is; linseed oil, the oil is poured into a tub or container to be heated. The linseed oil is brought up to a temperature of 200° F. The second ingredient is lanolin and it is stirred into the formula. The heat is turned off after the lanolin is blended in and melted. When the temperature cools to 150° F. the third ingredient; pine tar is added and blended in. After the pine tar is dissolved, the fourth ingredient; iodine is added and blended into the formula. The fifth ingredient is turpentine and it is blended in. When the temperature falls to 120° F. the sixth ingredient; hydrogen peroxide is blended in and last the seventh ingredient; copper sulphate is blended in to the formula.

The color of this invention is a deep brown pea soup. After the invention has cooled to room temperature it then can be bottled into plastic gallon containers, 55 gallon drums and the invention can be bottled into the preferred container; a 16 oz plastic bottle with a trigger spray nozzle on it for easy spraying.

Below is the formula by weight and the components:

| Component | Weight by percentage |
|---|---|
| Linseed Oil | .5585% |
| Lanolin | .0332 |
| Iodine | .0332 |
| Turpentine | .2695 |
| Hydrogen Peroxide | .030 |
| Pine Tar | .0703 |
| Copper Sulphate | .0053 |
| total | 1.00% |

This composition has demonstrated a 90–100% efficiency rate in preventive maintenance to hoofs over a five year period.

This invention has been tested and the test result were excellent, the test have been conducted over a wide area of the State of California, and the state of Oregon with great success. The lotion has been tested on 1500 horses, 500 head of cattle, 250 sheep, 300 goats, 25 mules and on Oxen, mules, donkeys and all with success of healing and great results of preservative to hoofs. In almost 100% of the cases of thrust a fungi, the problem completely disappeared. The Hoofs in 95% of the time prevented dryness to occur and in almost 100% of the application it repelled moist weather condition to the hoof.

The invention is fast acting and easy to apply by spraying onto and into and around the hoof. The ingredients in the invention drys quickly and preserves the hoof with softener conditioners, ointments, antiseptic, a disinfectants and a anti-fungi ingredient.

Various changes and or modifications may be made without departing from the spirit and scope of the invention described herein as will be apparent to those skilled in the art to which it pertains. It is accordingly intended that the present invention shall only be limited by the following claims.

We claim:

1. A composition exhibiting optimum effectiveness as a preventive or healing agent for animals with ungulates comprising on a weight basis linseed oil as a dispersing agent at 0.5585 percent; lanolin as a moisturizer at 0.0332 percent; turpentine as a drying agent at 0.2695 per cent; tincture of iodine at 0.0332 percent; pine tar as a sticking agent at 0.0703 per cent; hydrogen peroxide as an antibacterial agent at 0.03 percent and copper sulphate as a fungicidal agent at 0.0053 percent; 100 pound quantity of the composition is produced by heating 0.5585 pounds of linseed oil in a container to a temperature of 200° F. and combining 0.0332 pounds of lanolin; when the temperature drops to 150° F., 0.0703 pounds of pine tar, 0.0332 pounds of iodine and 0.2695 pounds of turpentine are combined, 0.030 pounds of hydrogen peroxide is combined when the temperature falls to 120° F. and 0.0053 pounds of copper sulphate is combined and when the temperature falls to 95° F., the said composition is ready to be added to a spray bottle to spray on and into ungulates.

* * * * *